(12) United States Patent
Chang (10) Patent No.: US 11,944,729 B1
(45) Date of Patent: Apr. 2, 2024

(54) LIFTABLE AROMA DIFFUSER

(71) Applicant: GOTRON E-COMMERCE INC, City Of Industry, CA (US)

(72) Inventor: Tiejun Chang, Harbin (CN)

( * ) Notice: Subject to any disclaimer, the term of this patent is extended or adjusted under 35 U.S.C. 154(b) by 0 days.

(21) Appl. No.: 18/317,413

(22) Filed: May 15, 2023

(51) Int. Cl.
*A61L 9/12* (2006.01)

(52) U.S. Cl.
CPC ........... *A61L 9/122* (2013.01); *A61L 2209/11* (2013.01); *A61L 2209/133* (2013.01)

(58) Field of Classification Search
None
See application file for complete search history.

(56) References Cited

U.S. PATENT DOCUMENTS

2017/0253338 A1* 9/2017 Fantuzzi ................ B64D 11/00

FOREIGN PATENT DOCUMENTS

CN 114508795 A * 5/2022

OTHER PUBLICATIONS

Chen et al. CN114508795A—translated document (Year: 2022).*

* cited by examiner

*Primary Examiner* — Jelitza M Perez (57) ABSTRACT

A liftable aroma diffuser includes a shell assembly having a storage space and a first opening communicated with the storage space; a lifting mechanism slidably connected to the shell assembly and including a lifting main body and a fragrance storage element arranged on the lifting main body and configured to bear a fragrance element; and a drive assembly arranged on the shell assembly and connected to the lifting main body and configured to drive the lifting mechanism to slide relative to the shell assembly. The lifting mechanism is able to change between a first received state of being received in the storage space and a first extended state of at least partially extending out of the storage space from the first opening.

18 Claims, 8 Drawing Sheets

LIFTABLE AROMA DIFFUSER

TECHNICAL FIELD

The present disclosure relates to the technical field of aroma diffusion, more particularly to a liftable aroma diffuser.

BACKGROUND

The working principle of an aroma diffuser is to decompose or vaporize essential oils and other fragrances, producing vapor that is dispersed into the air to adjust the scent of the environment.

Existing aroma diffusers generally diffuse the essential oils and other fragrances that are decomposed or vaporized inside the aroma diffusers into the air through fans. However, the existing aroma diffusers have a single diffusion mode in which the fragrance can only be slowly released from a single opening and the release speed cannot be increased.

SUMMARY

The present disclosure provides a liftable aroma diffuser, aiming to solve the problem that the existing aroma diffusers have a single diffusion mode in which the fragrance can only be slowly released from a single opening and the release speed cannot be increased.

The present disclosure provides a liftable aroma diffuser including: a shell assembly having a storage space and a first opening communicated with the storage space; a lifting mechanism slidably connected to the shell assembly and including a lifting main body and a fragrance storage element arranged on the lifting main body and configured to bear a fragrance element; and a drive assembly arranged on the shell assembly and connected to the lifting main body and configured to drive the lifting mechanism to slide relative to the shell assembly, so that the lifting mechanism is able to change between a first received state of being received in the storage space and a first extended state of at least partially extending out of the storage space from the first opening.

Further, the fragrance storage element is moveably connected to the lifting main body, so that the fragrance storage element can switch between a bearing state to bear the fragrance element and an accessible state convenient to access the fragrance element.

Further, the lifting main body further includes a substrate, two side plates and a transmission structure; the substrate is configured to slidably connect to the shell assembly, the two side plates are both connected to the substrate and are arranged opposite one another, the transmission structure is connected to the substrate and is connected to the drive assembly, and the fragrance storage element is located between the two side plates.

Further, the transmission structure includes a rack arranged along a lifting direction, the drive assembly further includes a drive housing, a motor main body and a gear wheel; the motor main body is received in the drive housing, the gear wheel is sleeved on an output shaft of the motor main body and is engaged with the rack.

Further, the fragrance storage element includes a rotating bracket and a pivot shaft, and the rotating bracket is rotatably fixed between the two side plates through the pivot shaft.

Further, the lifting mechanism further includes a second extended state of at least partially extending out of the storage space from the first opening, the lifting mechanism has a first extended height relative to the shell assembly in the first extended state, the lifting mechanism has a second extended height relative to the shell assembly in the second extended state, and the first extended height is different from the second extended height.

Further, in the second extended state, at least part of the fragrance storage element extends out of the storage space for the access of the fragrance element.

Further, the shell assembly includes an outer shell and an inner shell, the outer shell includes the storage space and the first opening, the inner shell and the drive assembly are both located in the storage space and the drive assembly is fixed on the inner shell, the inner shell includes a sliding cavity and a second opening communicated with the sliding cavity, and the lifting mechanism is slidably connected to the sliding cavity and can extend out from the second opening.

Further, the inner shell includes an inner shell main body and an air outlet plate connected to the inner shell main body and arranged around the second opening, the air outlet plate includes a plurality of air holes for discharging a fragrant gas released by the fragrance element.

Further the liftable aroma diffuser includes a first fan arranged in the storage space and located at a bottom of the inner shell main body, the inner shell main body and the outer shell enclose a first air passage, and one end of the first air passage corresponds to the first fan while the other end of the first air passage is configured to communicate with a part of the air holes.

Further, the liftable aroma diffuser includes a second fan, an inner part of the inner shell main body further includes a mounting cavity communicated with the other part of the air holes, and the second fan is arranged in the mounting cavity and is configured to output an air current toward the other part of the air holes.

Further, the liftable aroma diffuser includes a main circuit board arranged on the inner shell main body and located on one side opposite a back of the second fan.

Further, the liftable aroma diffuser includes a charging interface element arranged on the main circuit board, the outer shell includes a charging opening, and the charging interface element is arranged corresponding to the charging opening.

Further, the liftable aroma diffuser includes a control board, a cover plate and an electric connector, the lifting main body further includes a bearing plate connected to a top end of the substrate, the control plate is arranged on the bearing plate, the cover plate covers the control plate, the control plate is electrically connected to the cover plate through the electric connector, the cover plate includes at least one button area for a user to operate, the control plate is provided thereon with at least one control element corresponding to the button area, and the at least one control element is configured to be triggered to generate a control signal to control the operation of the liftable aroma diffuser.

Further, the electric connector is a flexible circuit board, and the flexible circuit board is adhered to a surface of the lifting main body.

Further, the control board is provided thereon with a light emitting element, the liftable aroma diffuser further includes a light guide ring adhered onto a bottom end of the bearing plate, and the light emitting element is configured to emit light toward the light guide ring.

Further, the at least one control element includes a switch control element configured to control the liftable aroma diffuser to switch between the first received state and the first extended state.

Further, the at least one control element further includes a fan control element configured to control the turn-on and turn-off of the first fan and the second fan.

Further, the at least one control element further includes a lifting control element configured to control the liftable aroma diffuser to switch between the first extended state and the second extended state.

Further, the outer shell further includes a first shell body and a second shell body, the first shell body is arranged on an upper end of the outer shell, and the second shell body is arranged on a lower end of the outer shell.

The beneficial effects of the present disclosure: a user can control the drive assembly through the shell assembly, thereby driving the lifting mechanism to slidably ascend and descend. Through the slidable lifting, the liftable aroma diffuser achieves the first received state and the first extended state. When the user is not to control the liftable aroma diffuser, the liftable aroma diffuser is in the first received state. The liftable aroma diffuser in the first received state does not release fragrance. When the user controls the liftable aroma diffuser to convert from the first received state into the first extended state, the drive assembly provides a transmission power to the lifting mechanism, so that the lifting mechanism slidably ascends. The liftable aroma diffuser in the first extended state starts to release fragrance, due to the extended height, the release speed of the fragrance can be increased. When the user controls the liftable aroma diffuser to convert from the first extended state into the first received state, the drive assembly provides a transmission power to the lifting mechanism, so that the lifting mechanism slidably descends. The liftable aroma diffuser in the first received state stops releasing fragrance.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

The present disclosure is further described below in detail in combination with the accompanying drawings and embodiments.

DETAILED DESCRIPTION OF THE EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the application, "a plurality of" means two or more, unless otherwise specifically defined.

Referring to FIG. 1 to FIG. 8, a liftable aroma diffuser according to one embodiment of the present disclosure is shown, including: a shell assembly 1 having a storage space and a first opening communicated with the storage space; a lifting mechanism 2 slidably connected to the shell assembly 1 and including a lifting main body 201 and a fragrance storage element 202 arranged on the lifting main body 201 and configured to bear a fragrance element; and a drive assembly 3 arranged on the shell assembly 1 and connected to the lifting main body 201 and configured to drive the lifting mechanism 2 to slide relative to the shell assembly 1, so that the lifting mechanism 2 can switch between a first received state of being received in the storage space and a first extended state of at least partially extending out of the storage space from the first opening.

Further, the shell assembly 1 is formed therein with the storage space and the first opening communicated with the storage space, providing a secure fixing structure for the liftable aroma diffuser. The lifting mechanism 2 is provided with the lifting main body 201 and the fragrance storage element 202 configured to bear the fragrance element, providing a lifting function for the liftable aroma diffuser and a storage structure to place a fragrance box. The drive assembly 3 is configured to provide a transmission function for the lifting mechanism 2, so that the lifting mechanism 2 can present the first received state or the first extended state.

Figure 1:
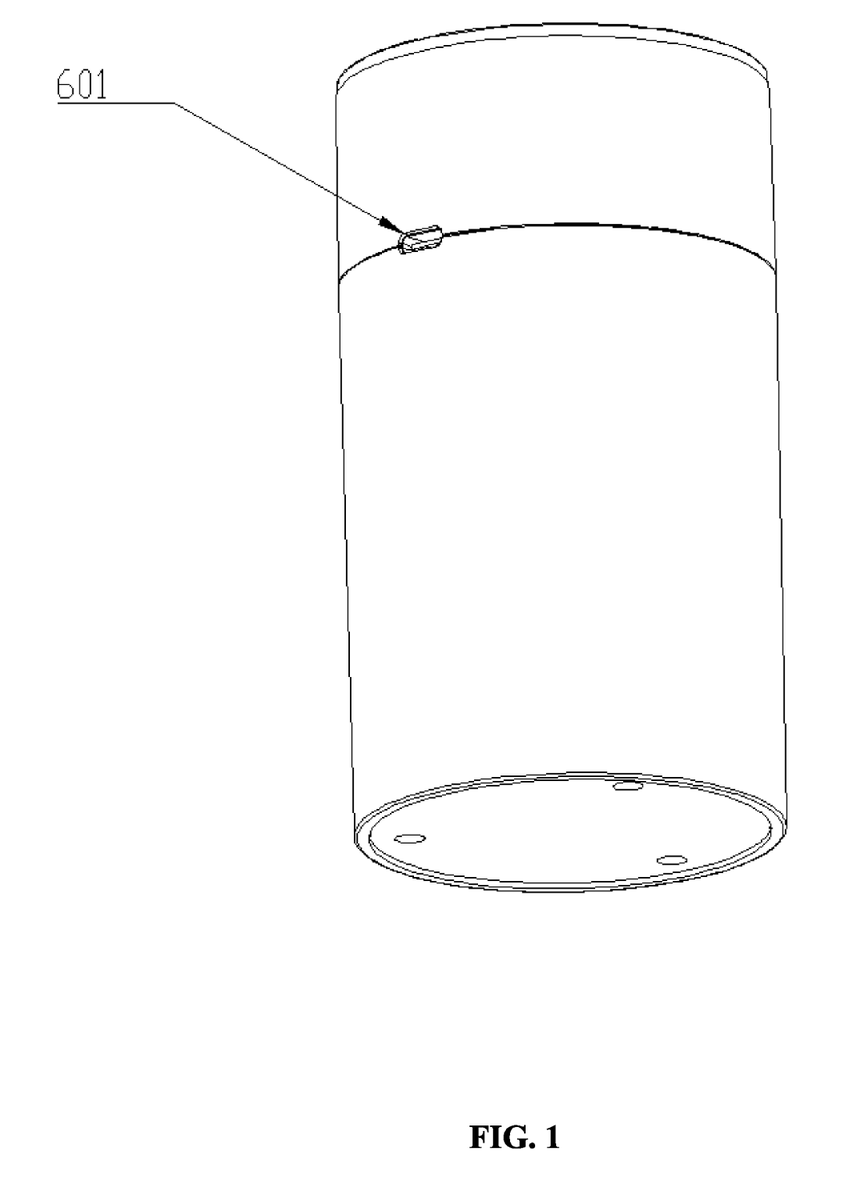
FIG. 1 is a perspective view of a liftable aroma diffuser of the present disclosure in a received state.
Figure 2:
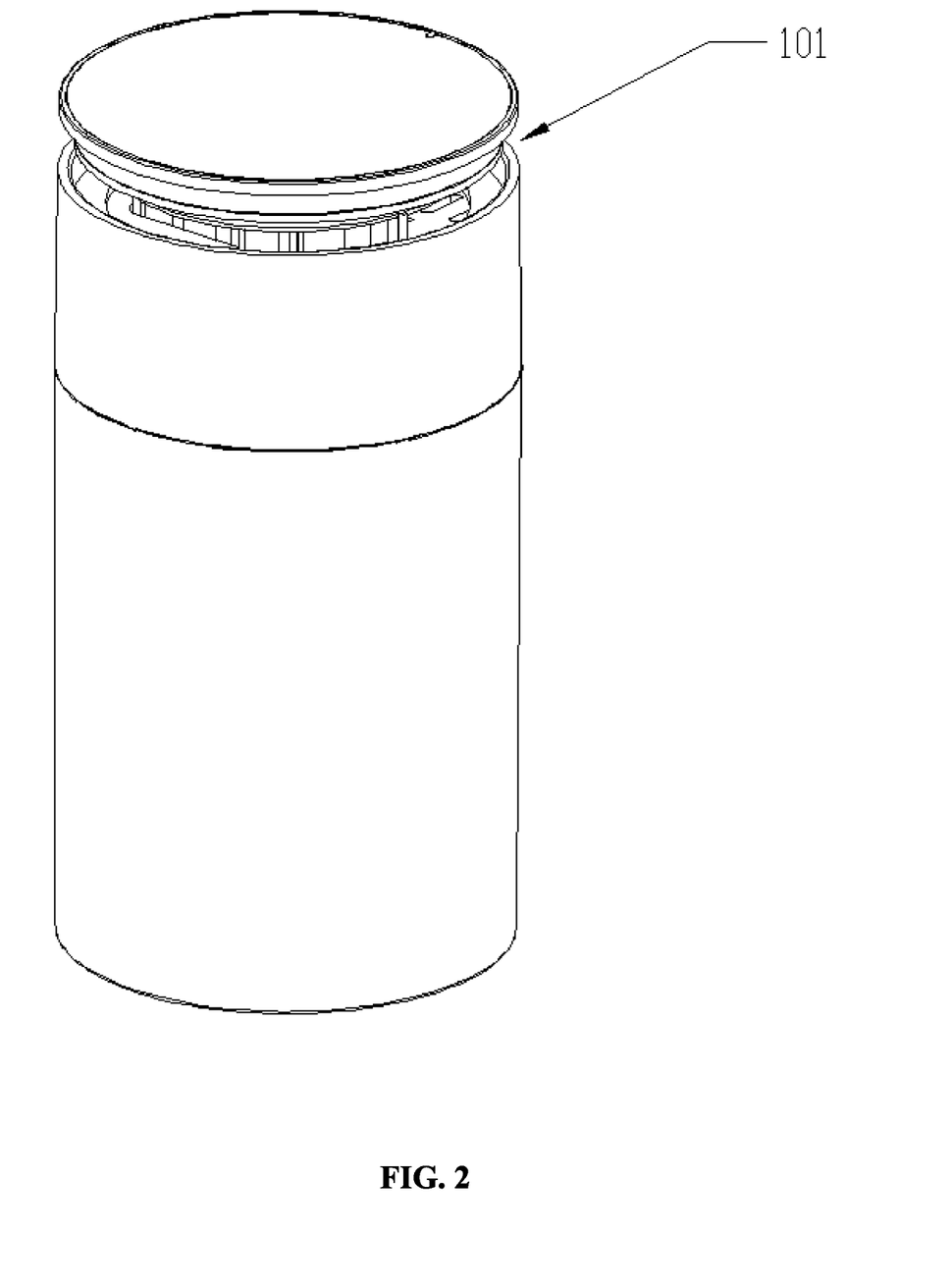
FIG. 2 is a perspective view of the liftable aroma diffuser of the present disclosure in a first extended state.
Figure 3:
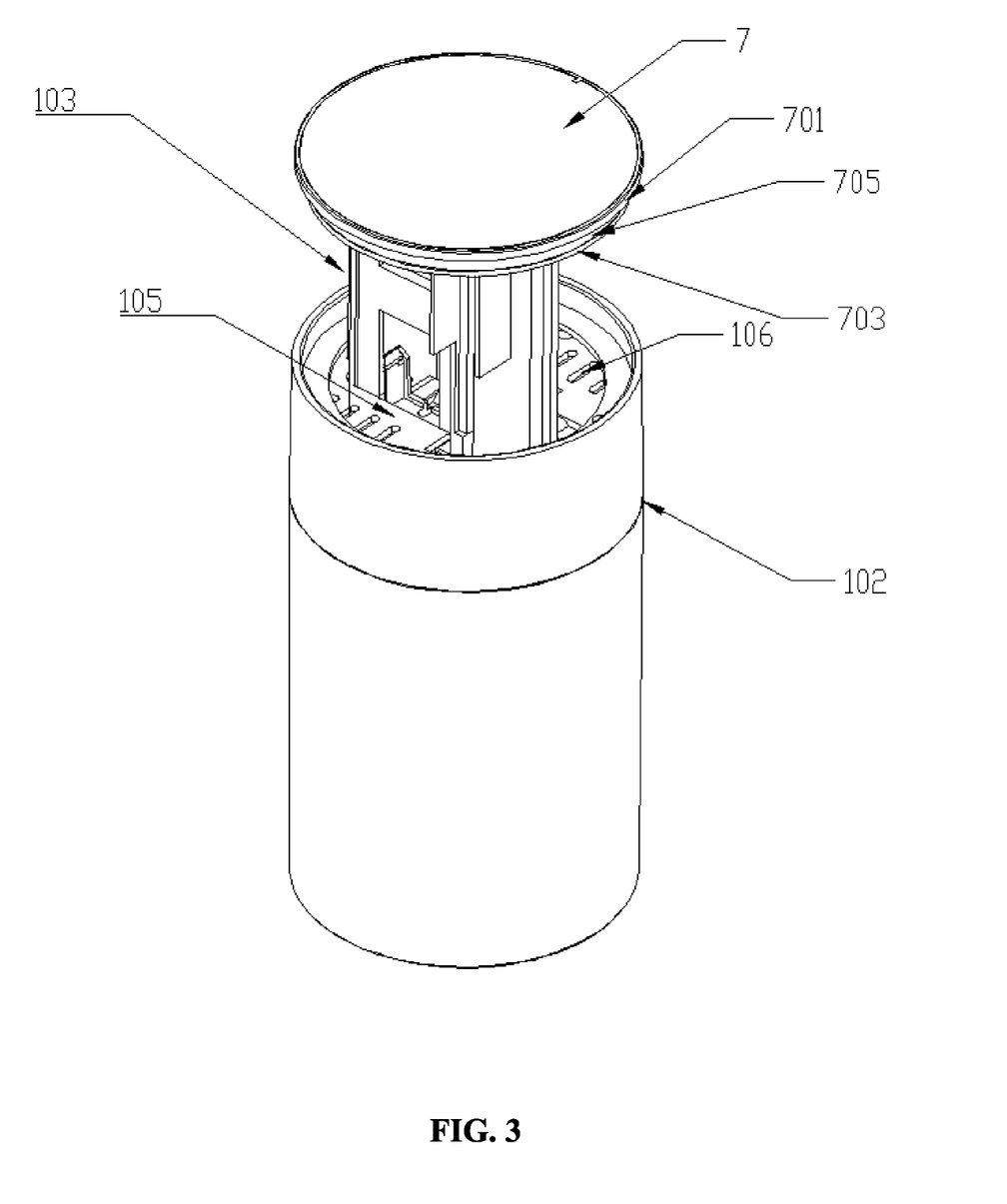
FIG. 3 is a perspective view of the liftable aroma diffuser of the present disclosure in a second extended state.
Figure 4:
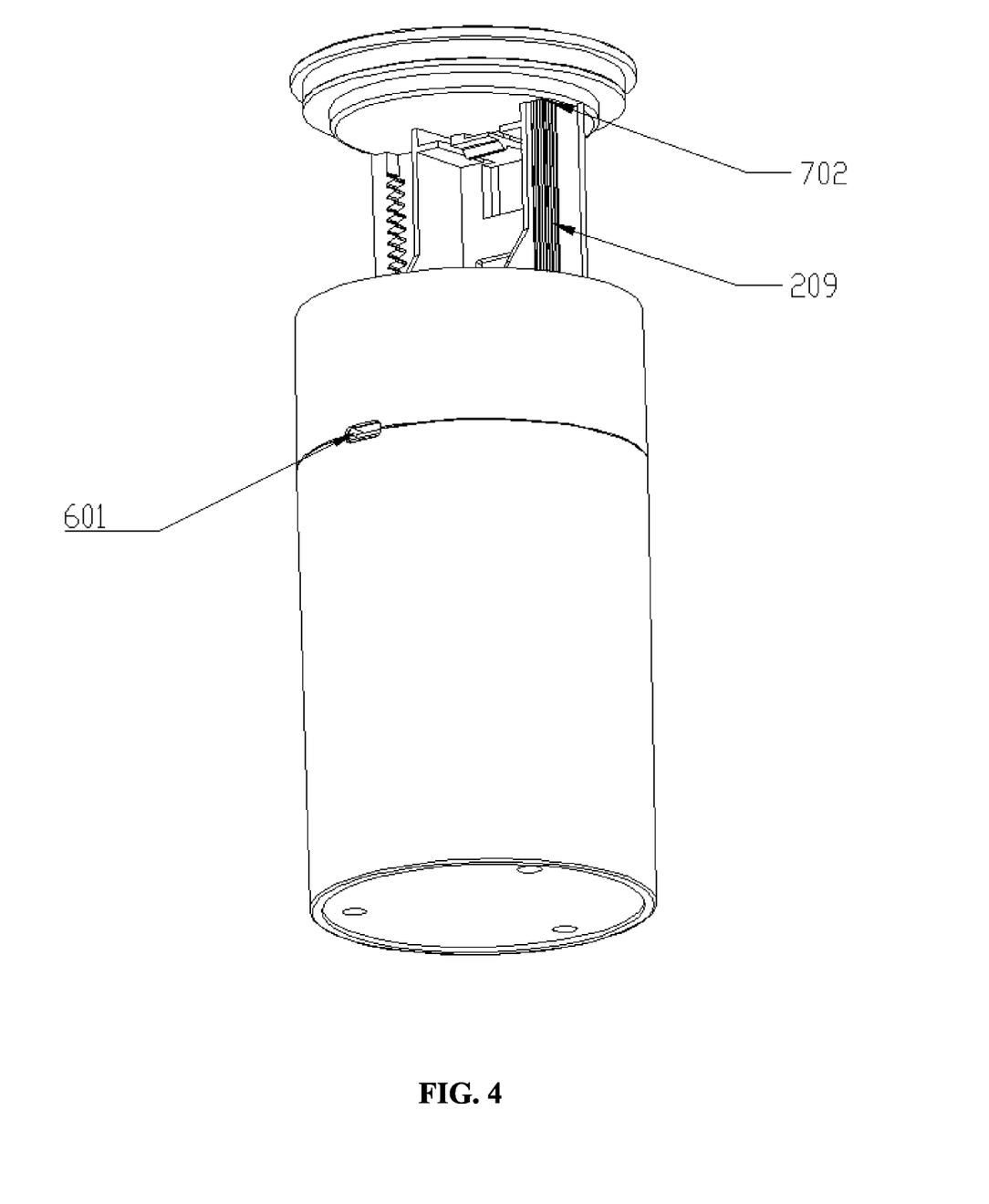
FIG. 4 is another perspective view of the liftable aroma diffuser of the present disclosure in the second extended state.
Figure 5:
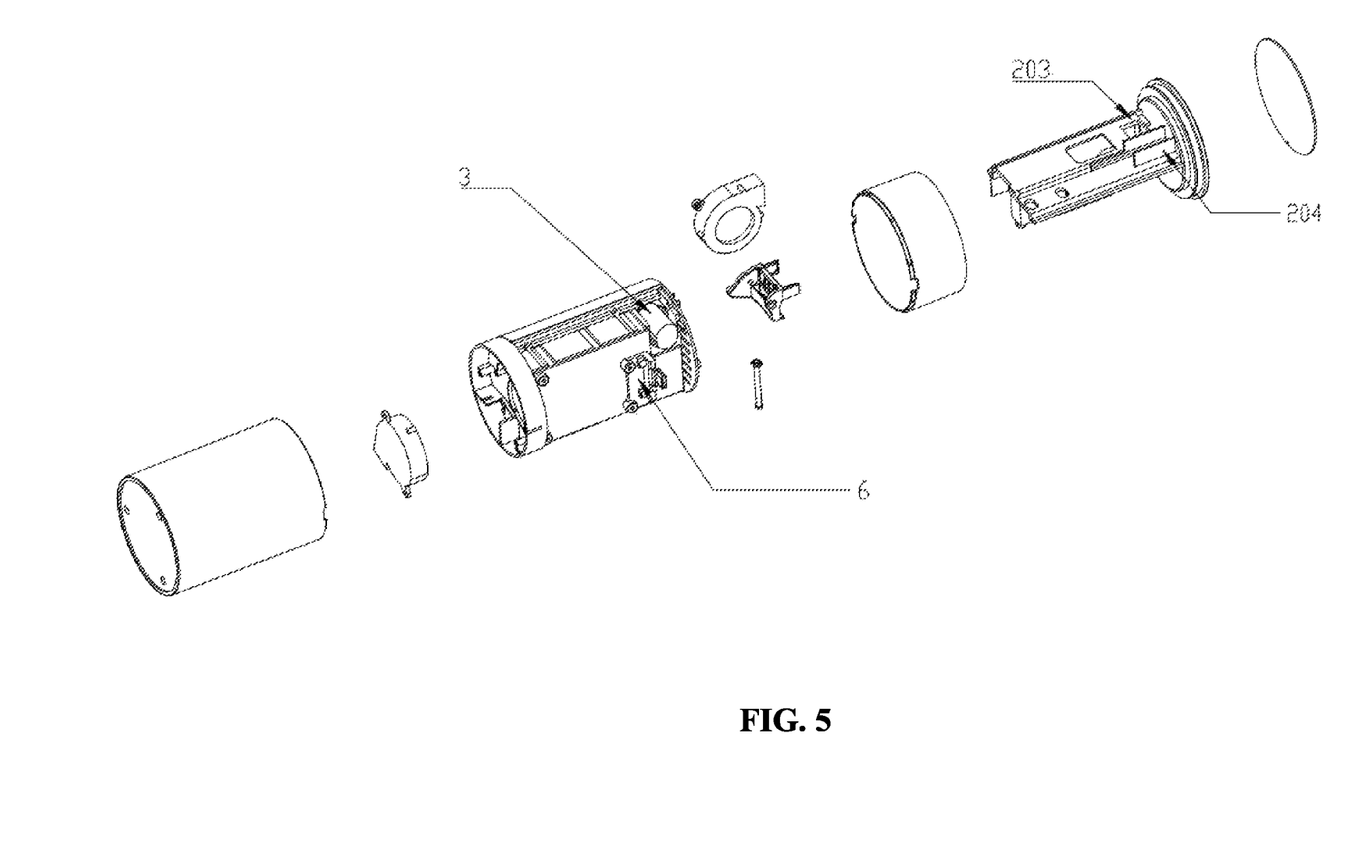
FIG. 5 is an exploded view of the liftable aroma diffuser of the present disclosure from another view.
Figure 6:
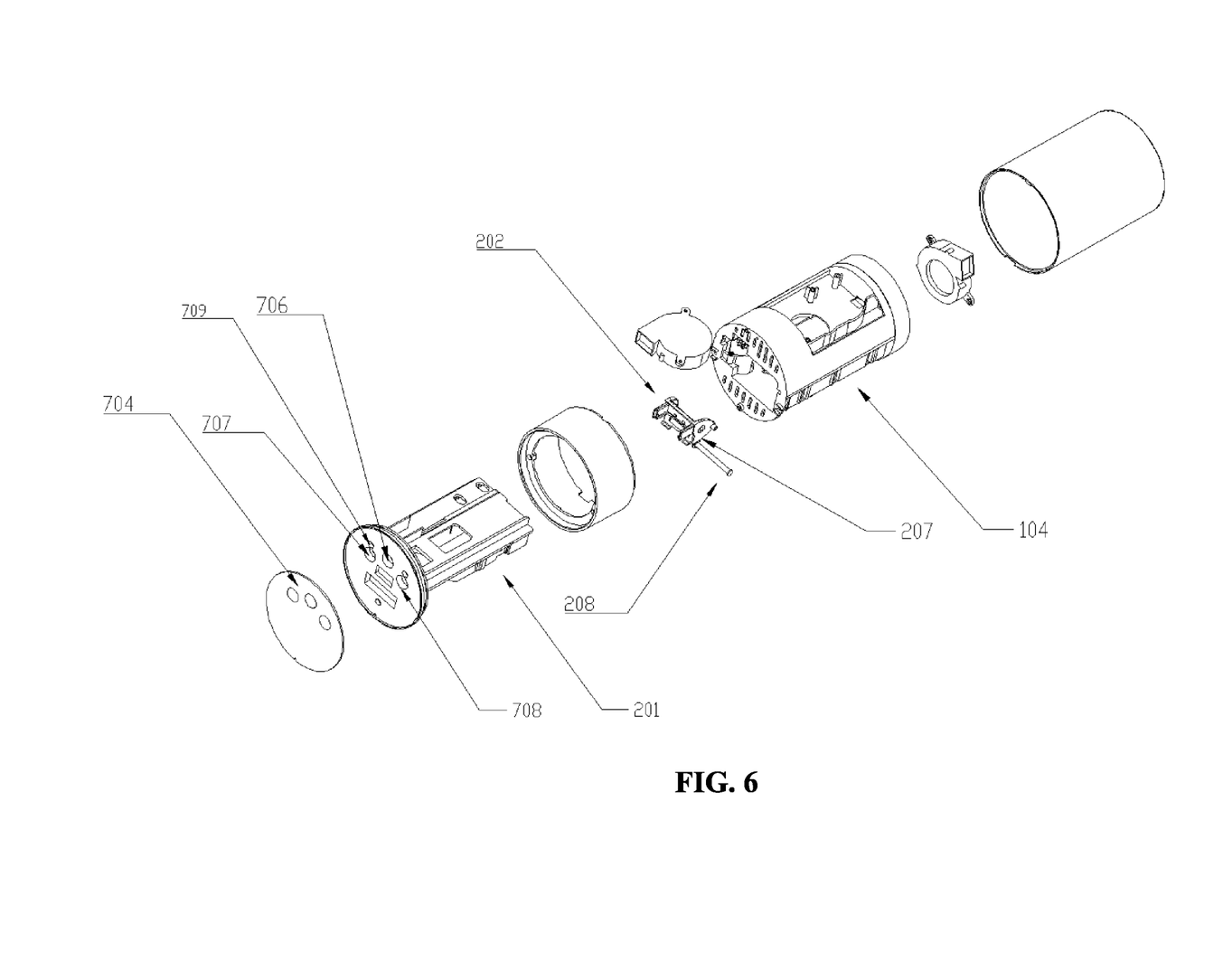
FIG. 6 is another exploded view of the liftable aroma diffuser of the present disclosure.
Figure 7:
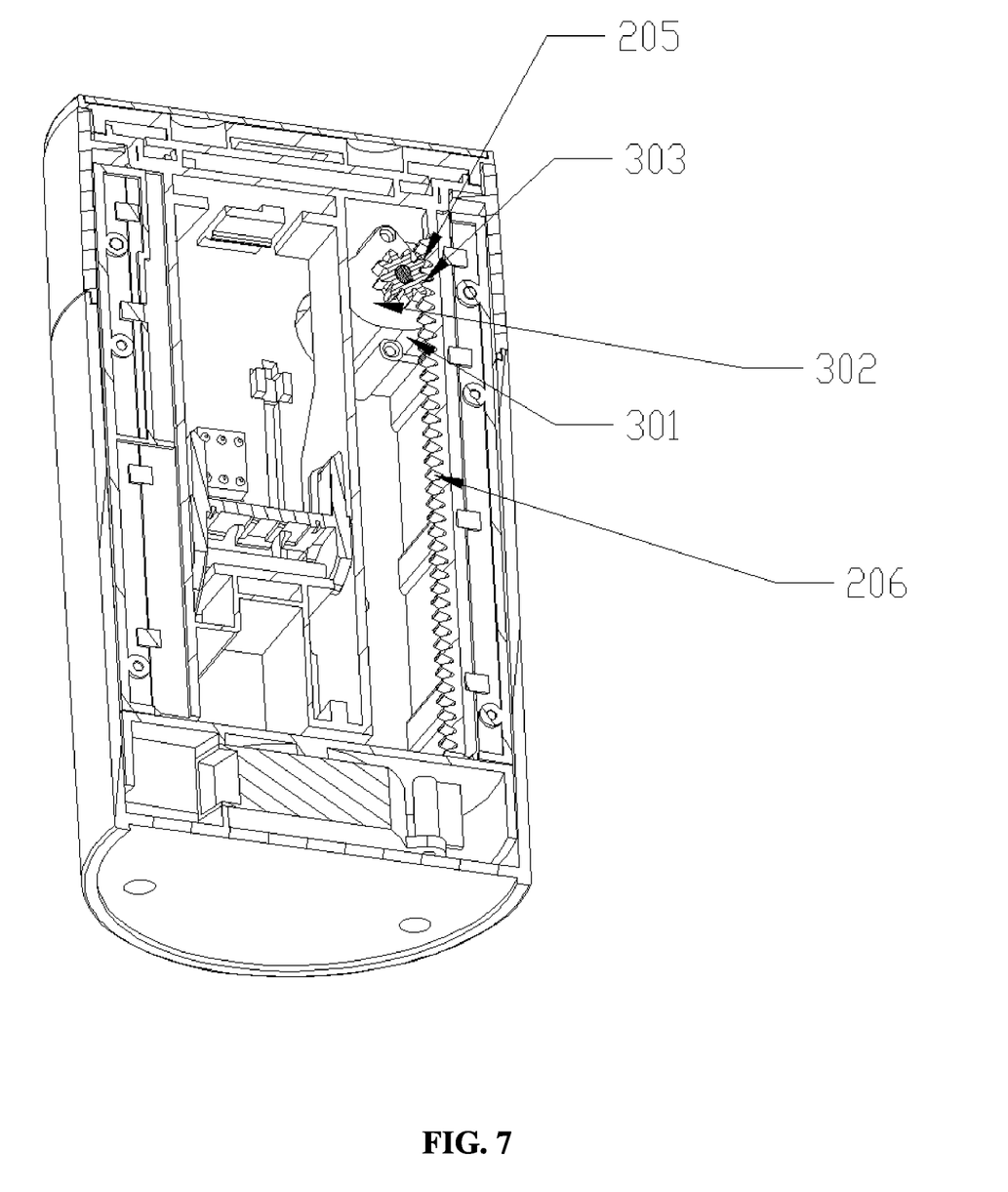
FIG. 7 is a perspective sectional view of the a liftable aroma diffuser of the present disclosure.
Figure 8:
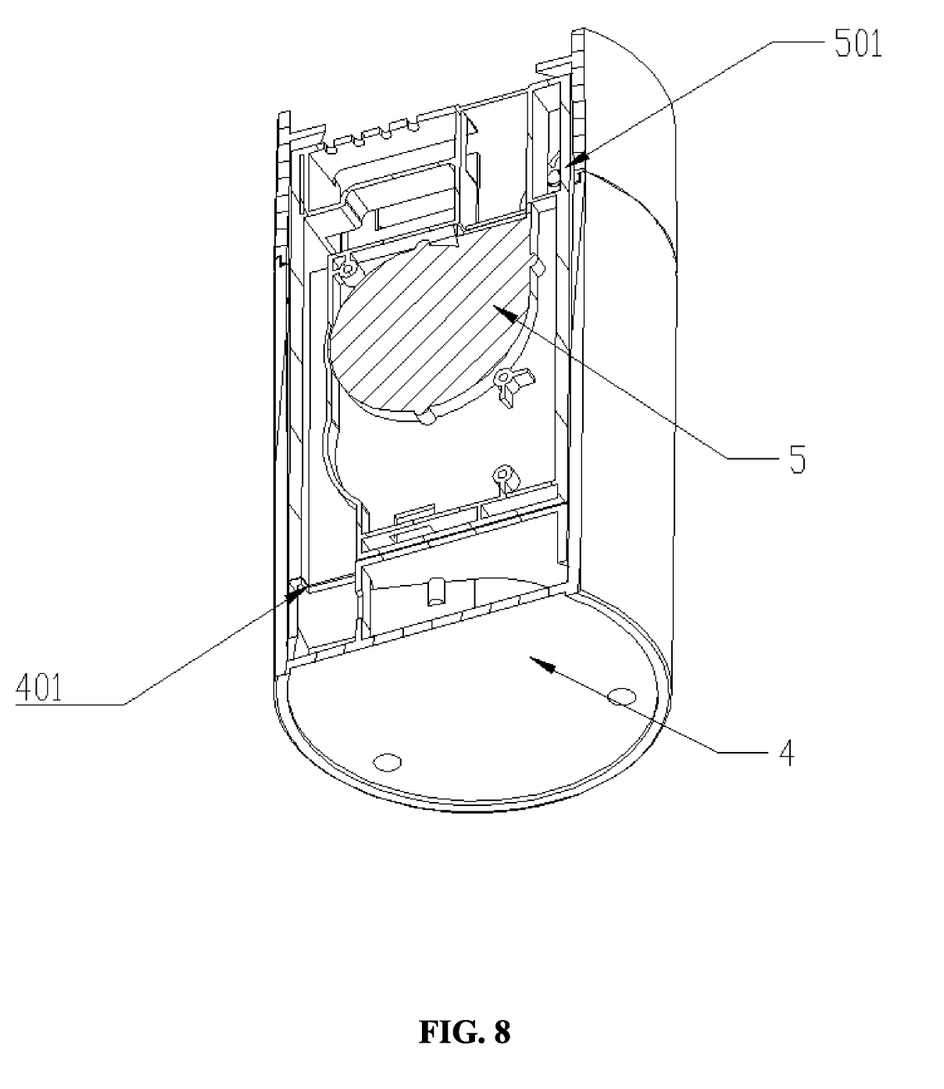
FIG. 8 is another perspective sectional view of a liftable aroma diffuser of the present disclosure.

When the lifting mechanism 2 is in the first received state, the liftable aroma diffuser is in a non-operating state. When the lifting mechanism 2 is in the first extended state, the liftable aroma diffuser is in an operating state.

Specifically, a user can control the drive assembly 3 through the shell assembly 1, thereby driving the lifting mechanism 2 to slidably ascend and descend. Through the slidable lifting, the liftable aroma diffuser achieves the first received state and the first extended state. When the user is not to control the liftable aroma diffuser, the liftable aroma diffuser is in the first received state. The liftable aroma diffuser in the first received state does not release fragrance. When the user controls the liftable aroma diffuser to convert from the first received state into the first extended state, the drive assembly 3 provides a transmission power to the lifting mechanism 2, so that the lifting mechanism 2 slidably ascends. The liftable aroma diffuser in the first extended state starts to release fragrance. When the user controls the liftable aroma diffuser to convert from the first extended state into the first received state, the drive assembly 3 provides a transmission power to the lifting mechanism 2, so that the lifting mechanism 2 slidably descends. The liftable aroma diffuser in the first received state stops releasing fragrance.

In the present embodiment, the fragrance storage element 202 is moveably connected to the lifting main body 201, so that the fragrance storage element 202 can switch between a bearing state to bear the fragrance element and an accessible state convenient to access the fragrance element.

Further, the lifting main body 201 is provided therein with the fragrance storage element 202 configured to bear and receive the fragrance element, which is convenient for a user to mount or replace the fragrance element in the liftable aroma diffuser.

Specifically, when a user needs to replace or mount the fragrance element, the user may control the lifting main body 201 to slidably ascend or slidably descend, then the fragrance storage element 202 arranged in the lifting main body 201 slidably ascends or slidably descends as well, whereby the user can conveniently replace or mount the fragrance element in the liftable aroma diffuser.

In the present embodiment, the lifting main body 201 further includes a substrate 203, two side plates 204 and a transmission structure 205. The substrate 203 is configured to slidably connect to the shell assembly 1. The two side plates 204 are both connected to the substrate 203 and are arranged opposite one another. The transmission structure 205 is connected to the substrate 203 and is connected to the drive assembly 3. The fragrance storage element 202 is located between the two side plates 204.

Further, the lifting main body 201 is provided therein with the substrate 203, the two side plates 204 and the transmission structure 205. The substrate 203 is configured to secure the lifting main body 201 into the lifting mechanism 2. The two side plates 204 are configured to securely hold a fragrance storage box in the lifting main body 201. The transmission structure 205 is configured to apply a transmission power to the lifting main body 201, so that the lifting main body 201 slidably ascends or slidably descends.

Specifically, when a user needs to mount or replace the fragrance element in the fragrance storage box, the user may control the drive assembly 3 to apply a transmission power to the lifting main body 201, so that the lifting main body 201 executes a command to slidably ascend, whereby the user can mount or replace the fragrance element in the fragrance storage box. When the user does not need to mount or replace the fragrance element in the fragrance storage box, the user may control the drive assembly 3 to apply a transmission power to the lifting main body 201, so that the lifting main body 201 executes a command to slidably descend, whereby the liftable aroma diffuser can protect the fragrance element.

In the present embodiment, the transmission structure 205 includes a rack 206 arranged along a lifting direction. The drive assembly 3 further includes a drive housing 301102, a motor main body 302 and a gear wheel 303. The motor main body 302 is received in the drive housing 301102. The gear wheel 303 is sleeved on an output shaft of the motor main body 302 and is engaged with the rack 206.

Further, the transmission structure 205 is provided thereon with a rolling rack 206 that moves along the lifting direction. The drive assembly 3 is provided therein with the drive housing 301102, the motor main body 302 and the gear wheel 303. The rolling rack 206 is configured to pull the lifting main body 201 to slidably ascend or slidably descend. The drive housing 301102 in the drive assembly 3 is configured to receive the motor main body 302. The motor main body 302 is configured to output a transmission power to the gear wheel 303. The gear wheel 303 is configured to engage with the rolling rack 206 and then receive the transmission power output by the motor main body 302, driving the rolling rack 206 to slidably ascend or slidably descend.

Specifically, when a user needs to convert the liftable aroma diffuser into the first received state or the first extended state, the user may control the drive assembly 3 to output a transmission power to the gear wheel 303 of the motor main body 302, so that the gear wheel 303 drives the rack 206 engaged with the rolling rack 206, controlling the lifting main body 201 to slidably ascend or slidably descend.

In the present embodiment, the fragrance storage element 202 includes a rotating bracket 207 and a pivot shaft 208. The rotating bracket 207 is rotatably fixed between the two side plates 204 through the pivot shaft 208.

Further, the fragrance storage element 202 is provided with the rotating bracket 207 and the pivot shaft 208. The rotating bracket 207 is configured to adjust the position to mount or replace the fragrance element. The pivot shaft 208 is configured to fix the rotating direction of the rotating bracket 207, so that the rotating bracket 207 can stably rotate back and forth in the fragrance storage box.

Specifically, when a user needs to adjust the fragrance element, the user may enable the lifting main body 201 of the liftable aroma diffuser to slidably ascend to the second extended state, so that the fragrance storage element 202 in the second extended state is presented to the user, whereby the user just needs to manually adjust the position of the rotating bracket 207 to mount or replace the fragrance element. When to replace an old fragrance element, the user just needs to rotate the rotating bracket 207 to take off the old fragrance element and mount a new fragrance element, and then rotate again the rotating bracket 207, whereby to complete replacing the fragrance.

In the present embodiment, the lifting mechanism 2 further includes a second extended state of at least partially extending out of the storage space from the first opening. The lifting mechanism 2 has a first extended height relative to the shell assembly 1 in the first extended state. The lifting mechanism 2 has a second extended height relative to the shell assembly 1 in the second extended state. The first extended height is different from the second extended height.

Further, the lifting mechanism 2 can extend out through the first opening to convert into the second extended state.

The second extended state is configured to completely present the fragrance storage box and the fragrance element in the lifting mechanism 2 to a user, whereby the user can timely mount or replace the fragrance element.

Specifically, when a user needs to adjust the fragrance element, the user may control the drive assembly 3 to output a transmission power to the lifting mechanism 2, so that the lifting mechanism 2 slidably ascends to the second extended state, presenting the fragrance storage element 202 and the fragrance element to the user, whereby the user can mount or replace the fragrance element. When the user has completed mounting or replacing the fragrance element, the user may control the drive assembly 3 to output a transmission power to the lifting mechanism 2, so that the lifting mechanism 2 slidably descends to the first extended state, where the liftable aroma diffuser can release fragrance.

In the present embodiment, in the second extended state, at least part of the fragrance storage element 202 extends out of the storage space for the access of the fragrance element.

Further, the lifting mechanism 2 can extend out through the first opening to convert into the second extended state. The second extended state is configured to completely present the fragrance storage box and the fragrance element in the lifting mechanism 2 to a user, whereby the user can timely mount or replace the fragrance element.

Specifically, when a user needs to adjust the fragrance element, the user may control the drive assembly 3 to output a transmission power to the lifting mechanism 2, so that the lifting mechanism 2 slidably ascends to the second extended state, presenting the fragrance storage element 202 and the fragrance element to the user, whereby the user can mount or replace the fragrance element. When the user has completed mounting or replacing the fragrance element, the user may control the drive assembly 3 to output a transmission power to the lifting mechanism 2, so that the lifting mechanism 2 slidably descends to the first extended state, where the liftable aroma diffuser can release fragrance.

In the present embodiment, the shell assembly 1 includes an outer shell 102 and an inner shell 103. The outer shell 102 includes the storage space and the first opening. The inner shell 103 and the drive assembly 3 are both located in the storage space and the drive assembly 3 is fixed on the inner shell 103. The inner shell 103 includes a sliding cavity and a second opening communicated with the sliding cavity. The lifting mechanism 2 is slidably connected to the sliding cavity and can extend out from the second opening.

Further, the storage space and the first opening provided for the outer shell 102 are configured to receive the inner shell 103 and the drive assembly 3. The inner shell 103 is configured to fixedly place the drive assembly 3. The sliding cavity and the second opening communicated with the sliding cavity are configured to enable the lifting mechanism 2 to convert into the first extended state or the second extended state through the second opening.

Specifically, when a user needs to enable the lifting mechanism 2 to slidably ascend or slidably descend, the user may enable the drive assembly 3 to output a transmission power to drive the lifting mechanism 2 to slidably ascend or slidably descend along the sliding cavity and the second opening communicated with the sliding cavity, so that the user can mount or replace the fragrance element. Further, the fragrance element can be exposed to the environment, enhancing the release efficiency of the fragrance element.

In the present embodiment, the inner shell 103 includes an inner shell main body 104 and an air outlet plate 105 connected to the inner shell main body 104 and arranged around the second opening. The air outlet plate 105 includes a plurality of air holes 106 for discharging a fragrant gas released by the fragrance element.

Further, the first fan 4 and the second fan 5 in the liftable aroma diffuser output an air current to the air outlet plate 105 through the air passage, improving the release efficiency of fragrance in the fragrance element. The air hole 106 is configured to further improve the release efficiency of fragrance in the fragrance element.

Specifically, when a user needs to accelerate the release of fragrance, the user may start a fan control element 707 in the liftable aroma diffuser. Through the fan control element 707, the first fan 4 and the second fan 5 are controlled to operate, outputting an air current to the air outlet plate 105 to improve the release efficiency of fragrance in the fragrance element. In addition, both sides of the air outlet plate 105 are provided with air outlets, so that a fragrant gas can be output by means of the air current and is uniformly released in the air environment.

In the present embodiment, the liftable aroma diffuser further includes a first fan 4 arranged in the storage space and located at a bottom of the inner shell main body 104. The inner shell main body 104 and the outer shell 102 enclose a first air passage 401. One end of the first air passage 401 corresponds to the first fan 4 while the other end of the first air passage 401 is configured to communicate with a part of the air holes 6.

Further, the first fan 4 is configured to output an air current from the bottom of the liftable aroma diffuser to the air outlet plate 105 through the first air passage 401. The air current is output from the liftable aroma diffuser to the air environment from the bottom up, effectively improving the release efficiency of fragrance in the fragrance element.

Specifically, when a user needs to accelerate the release of fragrance, the user may start the fan control element 707 in the liftable aroma diffuser. Through the fan control element 707, the first fan 4 is controlled to operate, outputting an air current from the bottom of the liftable aroma diffuser to the air outlet plate 105 from the bottom up, hence accelerating the volatilization of the unvolatilized fragrance into the environment.

In the present embodiment, the liftable aroma diffuser further includes a second fan 5. An inner part of the inner shell main body 104 further includes a mounting cavity communicated with the other part of the air holes 106. The second fan 5 is arranged in the mounting cavity and is configured to output an air current toward the other part of the air holes 106.

Further, the second fan 5 is configured to output an air current from one side of the liftable aroma diffuser to the air outlet plate 105 through a second air passage 501. The air current is output from the liftable aroma diffuser to the air environment upwardly from the side, effectively improving the release efficiency of fragrance in the fragrance element.

Specifically, when a user needs to accelerate the release of fragrance, the user may start the fan control element 707 in the liftable aroma diffuser. Through the fan control element 707, the second fan 5 is controlled to operate, outputting an air current from the bottom of the liftable aroma diffuser to the air outlet plate 105 upwardly from the side, hence accelerating the volatilization of the unvolatilized fragrance into the environment.

In the present embodiment, the liftable aroma diffuser further includes a main circuit board 6 arranged on the inner shell main body 104 and located on one side opposite a back of the second fan 5.

Further, the main circuit board 6 is configured to output a power to the drive assembly 3. Meanwhile, the main circuit board 6 is provided with a flexible circuit board 209 that is connected to a control plate 7 in the liftable aroma diffuser and configured to output a power to the control plate 7 so that a control element of the control plate 7 presents a corresponding light to a light guide ring 705 so that the light guide ring 705 emits lights.

Specifically, when a user needs to control the lifting mechanism 2 to slidably ascend or slidably descend, the main circuit board 6 first receives an external power supply input from a charting port and then converts it into an output power to output to the drive assembly 3 which then outputs a transmission power to the drive the lifting mechanism 2 to slidably ascend or slidably descend. Or, when a user needs to control the control plate 7 of the liftable aroma diffuser, the main circuit board 6 converts an external power supply input from a charging port into an output power which is output to the control plate 7 and the light guide ring 705 below the control plate 7 through the flexible circuit board 209, so that the control element in the control plate 7 presents the corresponding light.

In the present embodiment, the liftable aroma diffuser further includes a charging interface element arranged on the main circuit board 6. The outer shell 102 includes a charging opening 601, and the charging interface element is arranged corresponding to the charging opening 601.

Further, the charging interface element is configured to convert an external input power supply, and the charging opening 601 is configured to receive the external input power supply. An input power supply is received through the charging opening 601 and then is output through the charging interface element to the main circuit board 6, so that the liftable aroma diffuser can operate.

Specifically, when a user needs to use the liftable aroma diffuser, the user may insert an external input power port into the charging opening 601 of the liftable aroma diffuser, so that an input power supply is received into the charging interface element through the external input power port and then is output to the main circuit board 6 through the charging interface element, whereby being converted into a power supply of the liftable aroma diffuser. After successful conversion, the liftable aroma diffuser can normally operate.

In the present embodiment, the liftable aroma diffuser further comprises a control board 7, a cover plate 701 and an electric connector 702. The lifting main body 201 further includes a bearing plate connected to a top end of the substrate 203. The control plate 7 is arranged on the bearing plate, the cover plate 701 covers the control plate 7, and the control plate 7 is electrically connected to the cover plate 701 through the electric connector 702. The cover plate 701 includes at least one button area 704 for a user to operate. The control plate 7 is provided thereon with at least one control element 706-708 corresponding to the button area 704. The at least one control element 706-708 is configured to be triggered to generate a control signal to control the operation of the liftable aroma diffuser.

In the present embodiment, the electric connector 702 is a flexible circuit board 209, and the flexible circuit board 209 is adhered to a surface of the lifting main body 201.

Further, the flexible circuit board 209 is configured to receive an output power supply from the main circuit board 6 and output the power supply to the control board 7.

In the present embodiment, the control board 7 is provided thereon with a light emitting element 709. The liftable aroma diffuser further includes a light guide ring 705 adhered onto a bottom end of the bearing plate 703. The light emitting element 709 is configured to emit light toward the light guide ring 705. Further, the light emitting element 709 is configured to emit light toward the button area 704.

Specifically, when a user operates the at least one control element 706-708, both the button area 704 and the light guide ring 705 emit light to respond to the user operation.

In the present embodiment, the at least one control element includes a switch control element 706 configured to control the liftable aroma diffuser to switch between the first received state and the first extended state. The switch control element 706 is configured to control the liftable aroma diffuser to execute a command to convert into the first receive state and the first extended state. When the liftable aroma diffuser is in the first received state, the liftable aroma diffuser stops operating. When the liftable aroma diffuser is in the first extended state, the liftable aroma diffuser is in operation.

Specifically, when a user needs to control the liftable aroma diffuser to perform state conversion, the user may issue a switch control command to the liftable aroma diffuser through the switch control element 706, so that the liftable aroma diffuser is converted into the first received state or the first extended state. When the user needs to stop operating the liftable aroma diffuser, the liftable aroma diffuser is converted into the first received state through the switch control element 706, stopping releasing fragrance. When the user needs to start the liftable aroma diffuser, the liftable aroma diffuser is converted into the first extended state through the switch control element 706, starting to release fragrance.

In the present embodiment, the at least one control element further includes a fan control element 707 configured to control the turn-on and turn-off of the first fan 4 and the second fan 5. The fan control element 707 is configured to control the liftable aroma diffuser to execute a command to turn on or off the fan. When the liftable aroma diffuser starts the fan, the volatilization speed of the fragrance in the fragrance element is accelerated. When the fragrance element in the liftable aroma diffuser is used up or the user needs no volatilization of fragrance, the liftable aroma diffuser turns off the fan.

Specifically, when a user needs to control the fan of the liftable aroma diffuser to operate, the user may issue a fan control command to the liftable aroma diffuser through the fan control element 707, turning on the first fan 4 and the second fan 5. An air current is output from the liftable aroma diffuser through the first fan 4 and the second fan 5, accelerating the release and volatilization of the fragrance in the fragrance element. When the user needs no volatilization of fragrance, the user may also issue a fan control command to the liftable aroma diffuser through the fan control element 707, turning off the first fan 4 and the second fan 5.

In the present embodiment, the at least one control element further includes a lifting control element 708 configured to control the liftable aroma diffuser to switch between the first extended state and the second extended state. The lifting control element 708 is configured to control the liftable aroma diffuser to convert into the first extended state or the second extended state. When the liftable aroma diffuser is in the first extended state, the liftable aroma diffuser is in the fragrance release state. When the liftable aroma diffuser is in the second extended state, the liftable aroma diffuser is in the fragrance release state, meanwhile the fragrance storage element 202 and the fragrance element are presented to a user, whereby the user can mount or replace the fragrance element. After the fragrance element has been mounted or replaced, the second extended state can be adjusted back to the first extended state through the lifting control element 708.

Specifically, when a user needs to start the liftable aroma diffuser to mount or replace the fragrance, the user may issue a command to the liftable aroma diffuser by controlling the lifting control element 708, so that the liftable aroma diffuser is converted into the second extended state from the first extended state, presenting the fragrance storage element 202 and the fragrance element to the user, whereby the user can mount or replace the fragrance element. After the fragrance element has been mounted or replaced, the user may adjust the second extended state back to the first extended state through the lifting control element 708, whereby to complete mounting or replacing the fragrance.

In the present embodiment, the outer shell 102 further includes a first shell body and a second shell body. The first shell body is arranged on an upper end of the outer shell 102, and the second shell body is arranged on a lower end of the outer shell 102.

Further, the first shell is configured to secure and mount a lower end of the inner shell 103. The second shell is configured to secure an upper end of the inner shell 103. The first shell can be assembled with the second shell to form the outer shell 102. The outer shell 102 can secure and mount the entire inner shell 103.

As described above, one or more embodiments are provided in conjunction with the detailed description, The specific implementation of the present disclosure is not confirmed to be limited to that the description is similar to or similar to the method, the structure and the like of the present disclosure, or a plurality of technical deductions or substitutions are made on the premise of the conception of the present disclosure to be regarded as the protection of the present disclosure.

What is claimed is:

1. A liftable aroma diffuser, comprising:
a shell assembly having a storage space and a first opening communicated with the storage space;
a lifting mechanism slidably connected to the shell assembly and comprising a lifting main body and a fragrance storage element arranged on the lifting main body and configured to bear a fragrance element; and
a drive assembly arranged on the shell assembly and connected to the lifting main body and configured to drive the lifting mechanism to slide relative to the shell assembly, so that the lifting mechanism is able to change between a first received state of being received in the storage space and a first extended state of at least partially extending out of the storage space from the first opening,
wherein the lifting main body further comprises a substrate, two side plates and a transmission structure; the substrate is configured to slidably connect to the shell assembly, the two side plates are both connected to the substrate and are arranged opposite one another, the transmission structure is connected to the substrate and is connected to the drive assembly, and the fragrance storage element is located between the two side plates,
wherein the transmission structure comprises a rack arranged along a lifting direction, the drive assembly further comprises a drive housing, a motor main body and a gear wheel; the motor main body is received in the drive housing, the gear wheel is sleeved on an output shaft of the motor main body and is engaged with the rack.

2. The liftable aroma diffuser according to claim 1, wherein the fragrance storage element is moveably connected to the lifting main body, so that the fragrance storage element can switch between a bearing state to bear the fragrance element and an accessible state convenient to access the fragrance element.

3. The liftable aroma diffuser according to claim 1, wherein the fragrance storage element comprises a rotating bracket and a pivot shaft, and the rotating bracket is rotatably fixed between the two side plates through the pivot shaft.

4. A liftable aroma diffuser, comprising:
a shell assembly having a storage space and a first opening communicated with the storage space;
a lifting mechanism slidably connected to the shell assembly and comprising a lifting main body and a fragrance storage element arranged on the lifting main body and configured to bear a fragrance element; and
a drive assembly arranged on the shell assembly and connected to the lifting main body and configured to drive the lifting mechanism to slide relative to the shell assembly, so that the lifting mechanism is able to change between a first received state of being received in the storage space and a first extended state of at least partially extending out of the storage space from the first opening,
wherein the fragrance storage element is moveably connected to the lifting main body, so that the fragrance storage element can switch between a bearing state to bear the fragrance element and an accessible state convenient to access the fragrance element,
wherein the lifting mechanism further comprises a second extended state of at least partially extending out of the storage space from the first opening, the lifting mechanism has a first extended height relative to the shell assembly in the first extended state, the lifting mechanism has a second extended height relative to the shell assembly in the second extended state, and the first extended height is different from the second extended height.

5. The liftable aroma diffuser according to claim 4, wherein in the second extended state, at least part of the fragrance storage element extends out of the storage space for the access of the fragrance element.

6. A liftable aroma diffuser, comprising:
a shell assembly having a storage space and a first opening communicated with the storage space;
a lifting mechanism slidably connected to the shell assembly and comprising a lifting main body and a fragrance storage element arranged on the lifting main body and configured to bear a fragrance element; and
a drive assembly arranged on the shell assembly and connected to the lifting main body and configured to drive the lifting mechanism to slide relative to the shell assembly, so that the lifting mechanism is able to change between a first received state of being received in the storage space and a first extended state of at least partially extending out of the storage space from the first opening,
wherein the shell assembly comprises an outer shell and an inner shell, the outer shell comprises the storage space and the first opening, the inner shell and the drive assembly are both located in the storage space and the drive assembly is fixed on the inner shell, the inner shell comprises a sliding cavity and a second opening communicated with the sliding cavity, and the lifting mechanism is slidably connected to the sliding cavity and can extend out from the second opening.

7. The liftable aroma diffuser according to claim 6, wherein the inner shell comprises an inner shell main body and an air outlet plate connected to the inner shell main body and arranged around the second opening, the air outlet plate comprises a plurality of air holes for discharging a fragrant gas released by the fragrance element.

8. The liftable aroma diffuser according to claim 7, further comprising a first fan arranged in the storage space and located at a bottom of the inner shell main body, wherein the inner shell main body and the outer shell enclose a first air passage, and one end of the first air passage corresponds to the first fan while the other end of the first air passage is configured to communicate with a part of the air holes.

9. The liftable aroma diffuser according to claim 8, further comprising a second fan, wherein an inner part of the inner shell main body further comprises a mounting cavity communicated with the other part of the air holes, and the second fan is arranged in the mounting cavity and is configured to output an air current toward the other part of the air holes.

10. The liftable aroma diffuser according to claim 9, further comprising a main circuit board arranged on the inner shell main body and located on one side opposite a back of the second fan.

11. The liftable aroma diffuser according to claim 10, further comprising a charging interface element arranged on the main circuit board, wherein the outer shell comprises a charging opening, and the charging interface element is arranged corresponding to the charging opening.

12. The liftable aroma diffuser according to claim 8, further comprising a control board, a cover plate and an electric connector, wherein the lifting main body further comprises a bearing plate connected to a top end of the substrate, the control plate is arranged on the bearing plate, the cover plate covers the control plate, the control plate is electrically connected to the cover plate through the electric connector, the cover plate comprises at least one button area for a user to operate, the control plate is provided thereon with at least one control element corresponding to the button area, and the at least one control element is configured to be triggered to generate a control signal to control the operation of the liftable aroma diffuser.

13. The liftable aroma diffuser according to claim 12, wherein the electric connector is a flexible circuit board, and the flexible circuit board is adhered to a surface of the lifting main body.

14. The liftable aroma diffuser according to claim 12, wherein the control board is provided thereon with a light emitting element, the liftable aroma diffuser further comprises a light guide ring adhered onto a bottom end of the bearing plate, and the light emitting element is configured to emit light toward the light guide ring.

15. The liftable aroma diffuser according to claim 12, wherein the at least one control element comprises a switch control element configured to control the liftable aroma diffuser to switch between the first received state and the first extended state.

16. The liftable aroma diffuser according to claim 12, wherein the at least one control element further comprises a fan control element configured to control the turn-on and turn-off of the first fan and the second fan.

17. The liftable aroma diffuser according to claim 12, wherein the at least one control element further comprises a lifting control element configured to control the liftable aroma diffuser to switch between the first extended state and the second extended state.

18. The liftable aroma diffuser according to claim 1, wherein the shell assembly further comprises a first shell body and a second shell body, the first shell body is arranged on an upper end of the shell, and the second shell body is arranged on a lower end of the shell.

* * * * *